(12) United States Patent
Katsura et al.

(10) Patent No.: US 11,903,319 B2
(45) Date of Patent: Feb. 13, 2024

(54) METHOD OF MANUFACTURING AN ULTRASONIC PROBE

(71) Applicant: FUJIFILM HEALTHCARE CORPORATION, Kashiwa (JP)

(72) Inventors: Hidetsugu Katsura, Tokyo (JP); Yoshihiro Tahara, Tokyo (JP); Kazuhiro Kobayashi, Tokyo (JP)

(73) Assignee: FUJIFILM Healthcare Corporation, Kashiwa (JP)

( * ) Notice: Subject to any disclaimer, the term of this patent is extended or adjusted under 35 U.S.C. 154(b) by 0 days.

(21) Appl. No.: 17/742,857

(22) Filed: May 12, 2022

(65) Prior Publication Data
US 2022/0271216 A1 Aug. 25, 2022

Related U.S. Application Data

(62) Division of application No. 16/361,885, filed on Mar. 22, 2019, now Pat. No. 11,538,982.

(30) Foreign Application Priority Data

Aug. 22, 2018 (JP) .................................. 2018-155661

(51) Int. Cl.
*H10N 30/03* (2023.01)
*H10N 30/081* (2023.01)
(Continued)

(52) U.S. Cl.
CPC ............ *H10N 30/03* (2023.02); *A61B 8/4444* (2013.01); *A61B 8/4483* (2013.01); *H10N 30/02* (2023.02);
(Continued)

(58) Field of Classification Search
CPC ............... Y10T 29/42; Y10T 29/49121; Y10T 29/49005; A61B 8/4444; A61B 8/4483;
(Continued)

(56) References Cited

U.S. PATENT DOCUMENTS

| 5,586,914 A * | 12/1996 | Foster, Jr. | ......... Y10T 29/49121 29/827 |
| 5,592,730 A * | 1/1997 | Greenstein | ............ B06B 1/0622 29/25.35 |
| 5,920,145 A | 7/1999 | Wu et al. | |

FOREIGN PATENT DOCUMENTS

| JP | 2003-348693 A | 12/2003 |
| JP | 2009-260481 A | 11/2009 |

(Continued)

OTHER PUBLICATIONS

Takeuchi et, "Novel 1-3 piezo-composites using synchrotron radiation lithography and its application for high frequency medical imaging arrays," 1997 IEEE Ultrasonics Symposium Proceedings. An International Symposium (Cat. No.97CH36118), Toronto, ON, Canada, 1997, pp. 919-922. (Year: 1997).*

(Continued)

*Primary Examiner* — A. Dexter Tugbang
(74) *Attorney, Agent, or Firm* — Crowell & Moring LLP

(57) ABSTRACT

The present invention is directed to improving an insulating property of a backing in which a lead array is buried. The method includes a coating forming process, in which insulating coatings are formed with respect to at least a plurality of lead rows included in a plurality of lead frames; after the forming of the insulating coatings, a plate manufacturing process, in which a plurality of backing plates are manufactured by pouring a backing material towards a lead row in each of the plurality of lead frames so that the lead row and the backing material are integrated with each other; and a laminating process, in which the plurality of backing plates are laminated.

3 Claims, 14 Drawing Sheets

(51) Int. Cl.
*A61B 8/00* (2006.01)
*H10N 30/02* (2023.01)
*H10N 30/084* (2023.01)
*G01N 29/22* (2006.01)

(52) U.S. Cl.
CPC ......... *H10N 30/081* (2023.02); *H10N 30/084* (2023.02); *G01N 29/226* (2013.01); *Y10T 29/42* (2015.01); *Y10T 29/49005* (2015.01); *Y10T 29/49121* (2015.01)

(58) Field of Classification Search
CPC ....... H01L 41/23; H01L 41/25; H01L 41/331; H01L 41/333; G01N 29/226; H10N 30/02; H10N 30/03; H10N 30/081; H10N 30/084
See application file for complete search history.

(56) References Cited

FOREIGN PATENT DOCUMENTS

| | | | | |
|---|---|---|---|---|
| JP | 2014183858 A | * | 10/2014 | ........... A61B 8/4444 |
| JP | 2015-228932 A | | 12/2015 | |
| JP | 2018027235 A | * | 2/2018 | |

OTHER PUBLICATIONS

United States Non-Final Office Action issued in U.S. Appl. No. 16/361,885 dated Jul. 6, 2022 (nine (9) pages).
English translation of document B2 (JP 2003-348693 A filed on May 12, 2022) (six (6) pages).
Bae, Byungkuk, et al. "Development of a Highly Attenuative Backing for Ultrasonic Transducers with Periodic Arrangement of Polymeric Rods Inside the Backing," 2013 IEEE International Ultrasonics Symposium (IUS), 2013, pp. 1105-1108 (four (4) pages).

* cited by examiner

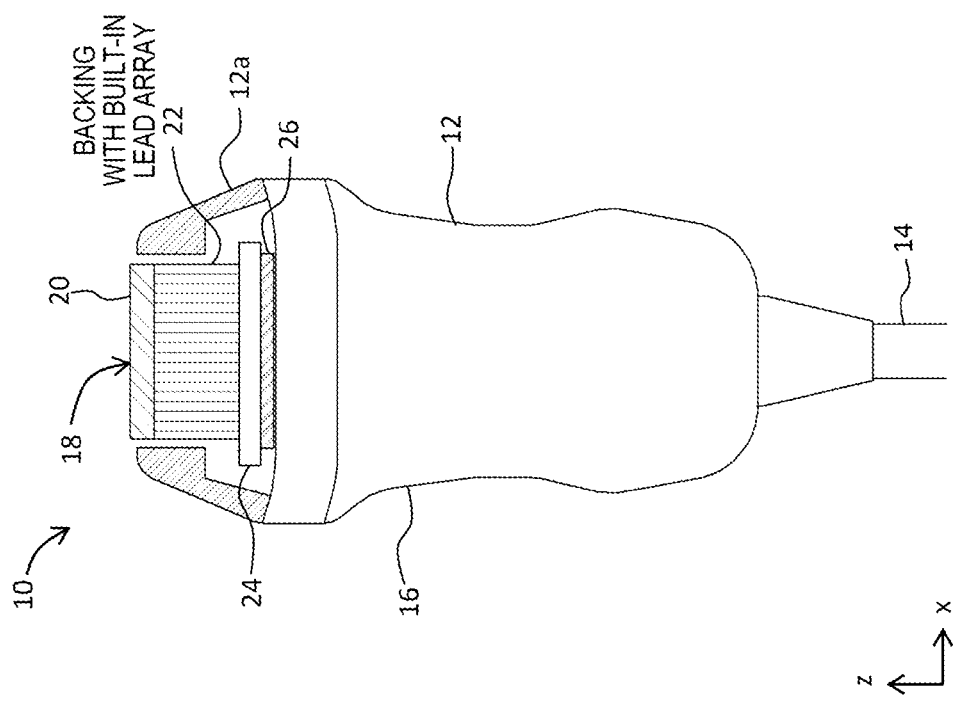

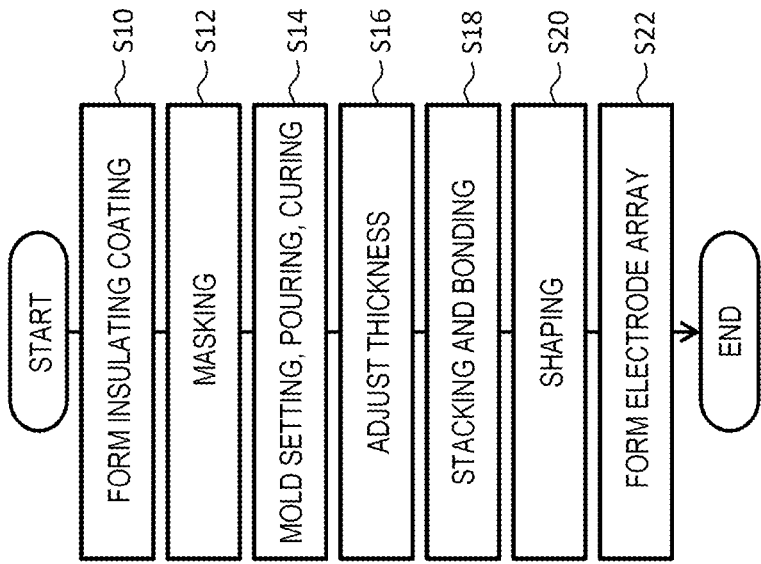

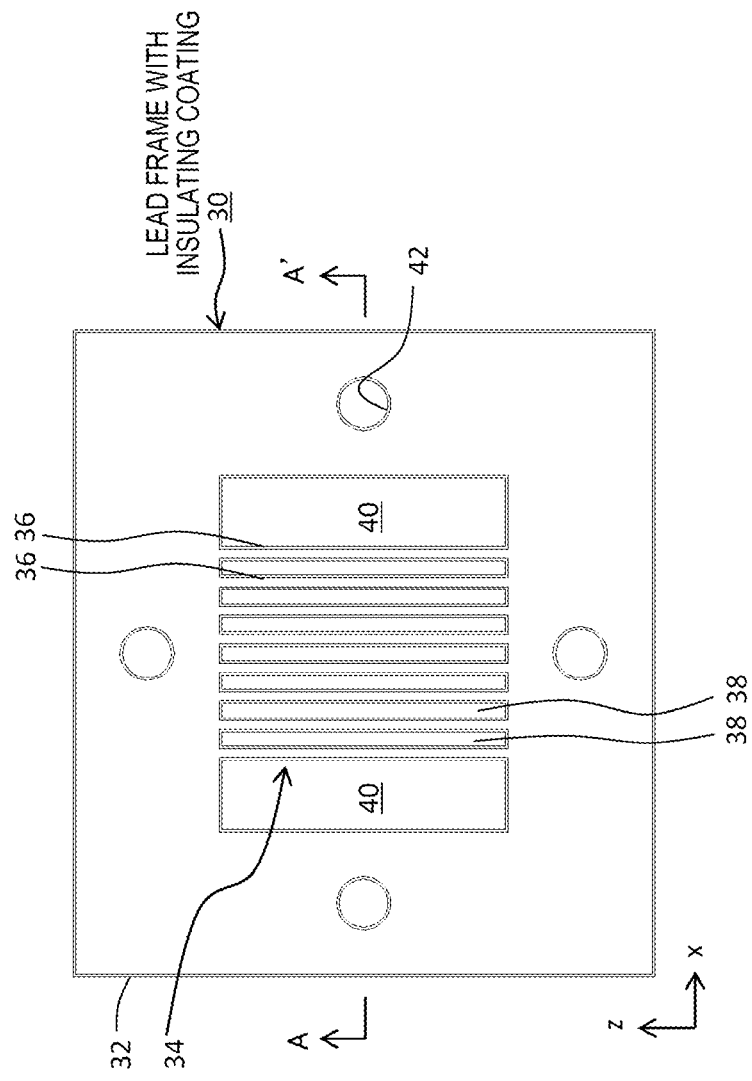
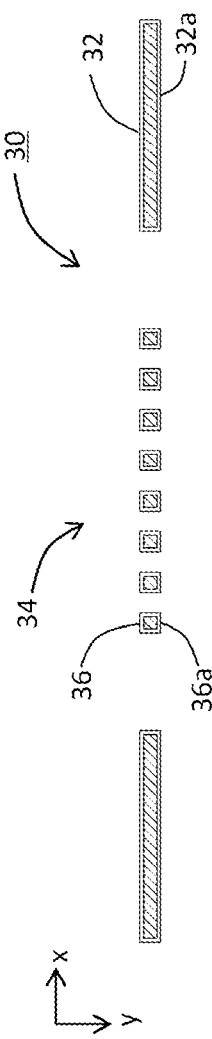

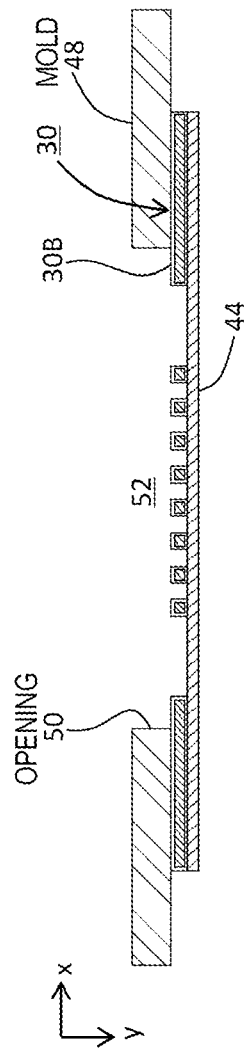
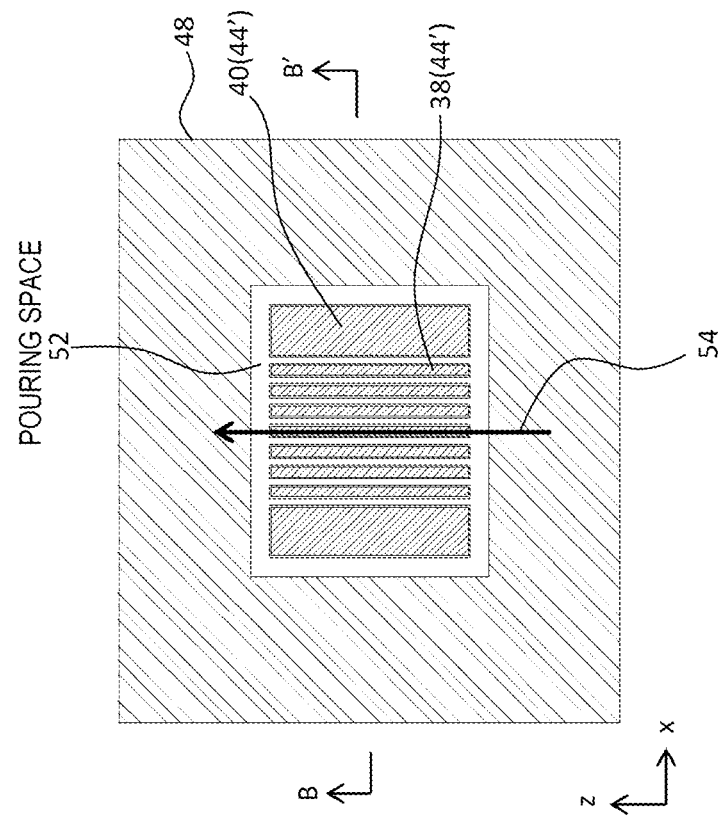

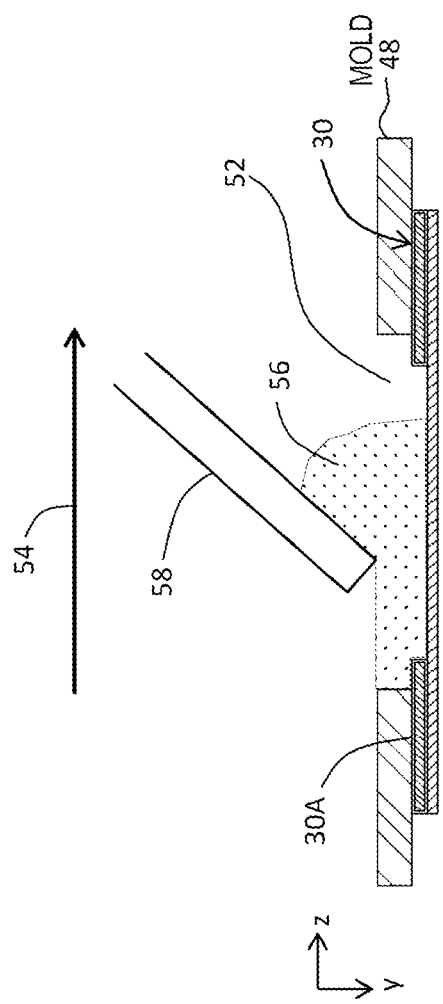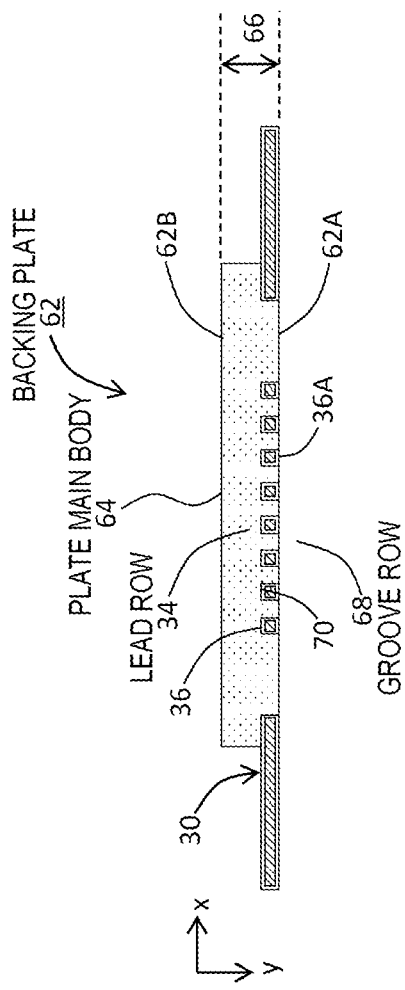

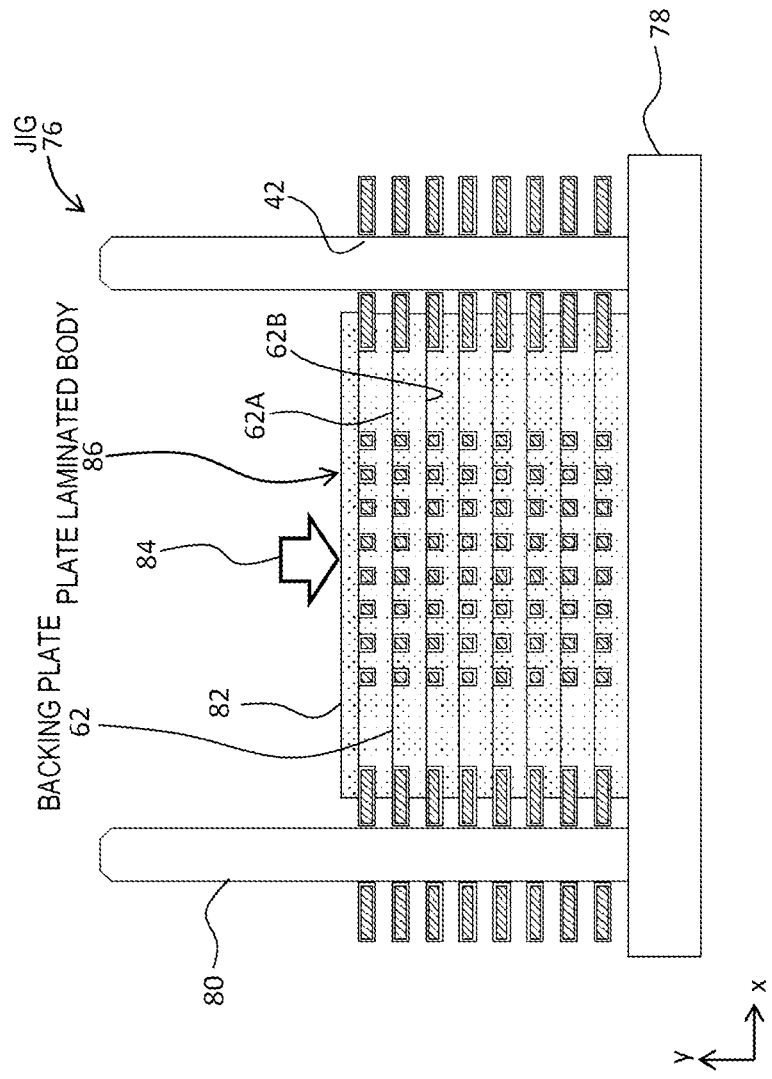

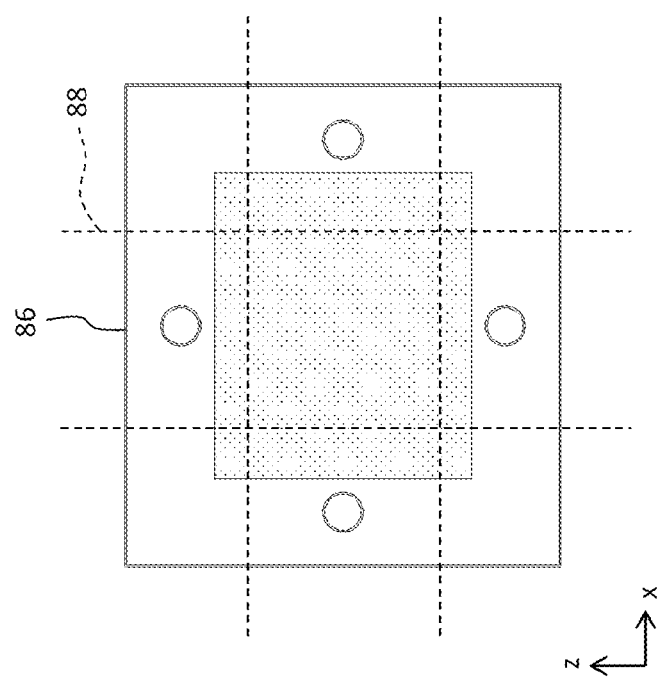

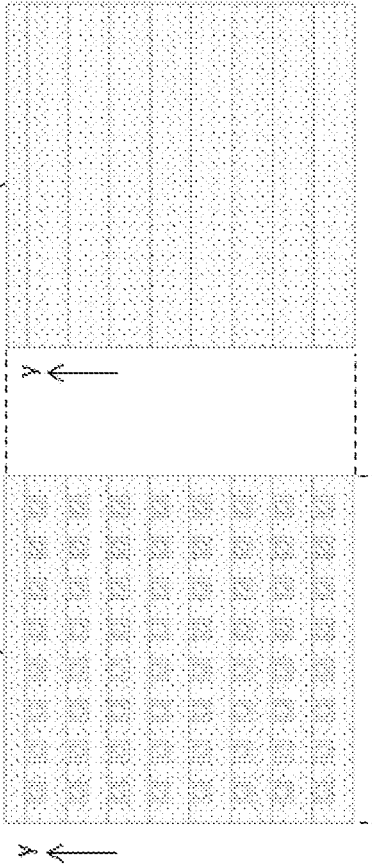
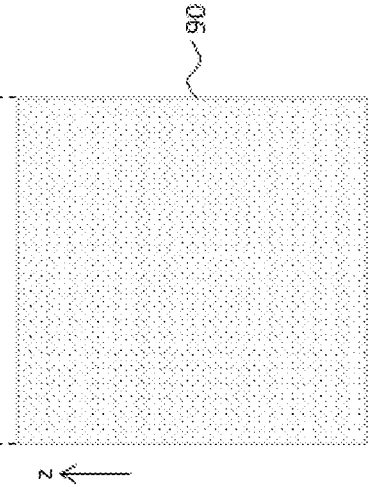
FIG. 13A
FIG. 13B
FIG. 13C

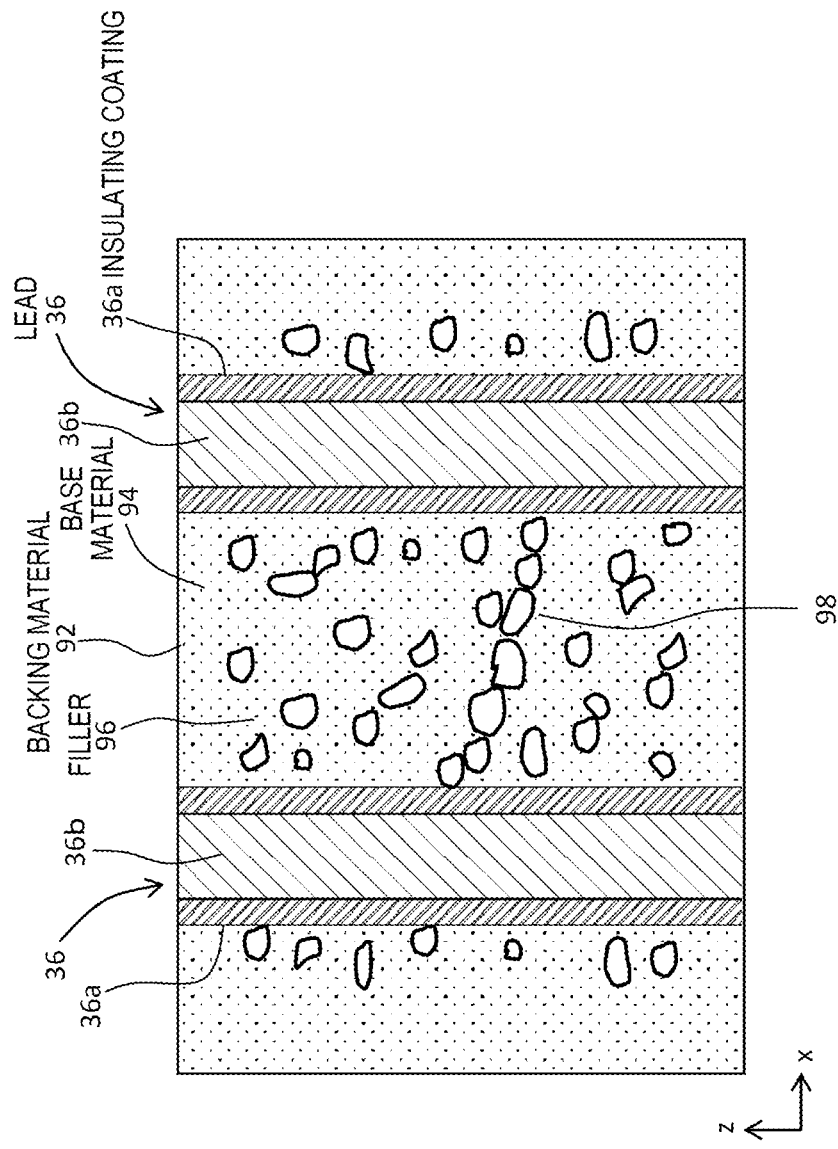

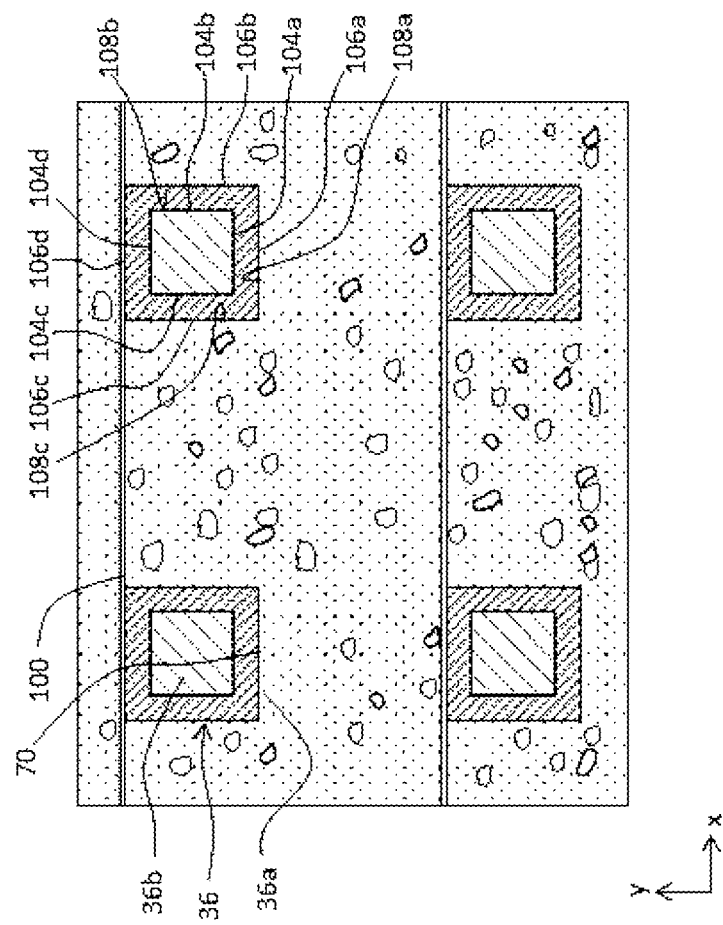

METHOD OF MANUFACTURING AN ULTRASONIC PROBE

CROSS REFERENCE TO RELATED APPLICATIONS

This application is a divisional of U.S. patent application Ser. No. 16/361,885, filed Mar. 22, 2019, which claims priority to Japanese Patent Application No. 2018-155661, filed Aug. 22, 2018, the disclosures of all of which are expressly incorporated by reference herein.

BACKGROUND OF THE INVENTION

1. Field of the Invention

The present invention relates to an ultrasonic probe and a method of manufacturing a backing, and more particularly, to a structure and manufacturing method of a backing including a lead array.

2. Description of Related Art

A 3D probe is used to obtain volume data from a three-dimensional space in a living body. A 3D probe is an ultrasonic probe and includes a two-dimensional vibration element array (2D vibration element array). A two-dimensional vibration element array consists of, for example, hundreds, thousands, or several tens of thousands of vibration elements that are arranged two-dimensionally.

A backing including a lead array is arranged on a rear surface side (non-living body side) of a two-dimensional vibration element array in order for a plurality of signal lines to be connected to a plurality of vibration elements configuring the two-dimensional vibration element array (see JP-A-2015-228932). It is also referred to as a backing with built-in lead array. The backing is formed of a backing material that scatters or absorbs ultrasonic waves emitted from the two-dimensional vibration element array to the rear surface side. The backing material includes a mother material (base material) and one or a plurality of fillers for achieving a desired acoustic characteristic. The base material generally includes a material having an insulating property. Some of the filler has conductivity. According to the related art, each lead in the backing is formed of a simple copper wire, etc. without being coated.

JP-A-2003-348693 discloses a backing having a specified structure formed by intensively arranging a plurality of composites. Each of the composites includes a lead wire and an attenuation layer covering the lead wire. JP-A-2003-348693 also discloses that an insulating layer is provided on an outer side of the lead wire (between the lead wire and the attenuation layer).

As described above, some of fillers included in the backing material may have the conductive property. When each lead wire is arranged in the backing in a state of being exposed, the insulating property of the backing may be deteriorated. In detail, for example, when a filling rate of the filler is high, there is a concern about short-circuits due to a string of filler particles among the leads. In addition, in a case where the backing includes a laminated structure including a plurality of backing plates, there is a risk of generating ion migration, etc. between the backing plates (interface). The ion migration is a phenomenon that degrades the insulating property due to ions that are generated by moisture entering the interface and contaminants existing on the interface.

When the backing is formed as a laminated structure including the plurality of backing plates, an adhesive is used to bond the plurality of backing plates. In order to prevent degradation in the backing effect, it is desirable to reduce a usage amount of the adhesive.

SUMMARY OF THE INVENTION

The present invention is to improve an insulating property of a backing in which a lead array is buried. The present invention is to decrease an amount of an adhesive that is used in manufacturing of a backing, in which a lead array is buried, and remains after the manufacturing.

An ultrasonic probe according to the present invention includes: an vibration element array consisting of a plurality of vibration elements arranged two-dimensionally; and a backing provided on a rear surface side of the vibration element array and consisting of a plurality of backing plates that are laminated, wherein each of the backing plates includes: a lead row consisting of a plurality of leads that are electrically connected to the vibration element array; and a plate main body formed of a backing material, the plate main body including a plurality of grooves that are directly coupled to the plurality of leads without an adhesive layer while accommodating the plurality of leads, and each of the leads includes a lead wire and an insulating coating wrapping the lead wire.

A method of manufacturing a backing according to the present invention includes: a coating forming process, in which insulating coatings are formed with respect to at least a plurality of lead rows included in a plurality of lead frames; after the forming of the insulating coatings, a plate manufacturing process, in which a plurality of backing plates are manufactured by pouring a backing material towards a lead row in each of the plurality of lead frames so that the lead row and the backing material are integrated with each other; and a laminating process, in which the plurality of backing plates are laminated.

According to the present invention, an insulating property of a backing in which a lead array is buried may be improved. According to the present invention, an amount of an adhesive that is used in manufacturing of a backing, in which a lead array is buried, and remains after the manufacturing may be decreased.

BRIEF DESCRIPTION OF THE DRAWINGS

FIG. 1 is a schematic diagram showing an ultrasonic probe according to an embodiment;

FIG. 2 is a flowchart illustrating a method of manufacturing a backing according to an embodiment;

FIG. 3 is a front view of a lead frame with an insulating coating;

FIG. 4 is a cross-sectional view of a lead frame with an insulating coating;

FIG. 6 is a cross-sectional view of a lead frame with an insulating coating, on which a mold is arranged;

FIG. 7 is a top view of a lead frame with an insulating coating, on which a mold is arranged;

FIG. 8 is a cross-sectional view showing pouring and molding of a backing material;

FIG. 9 is a cross-sectional view of a backing plate;

FIG. 11 is a diagram of a plate laminated body;

FIG. 12 is a diagram showing a cut line with respect to a plate laminated body;

FIGS. 13A to 13C are diagrams of a backing, in which a lead array is buried;

FIG. 14 is a schematic diagram showing a vertical section of a backing;

FIG. 15 is a schematic diagram showing a horizontal section of a backing;

DESCRIPTION OF EMBODIMENTS

Figure 5:
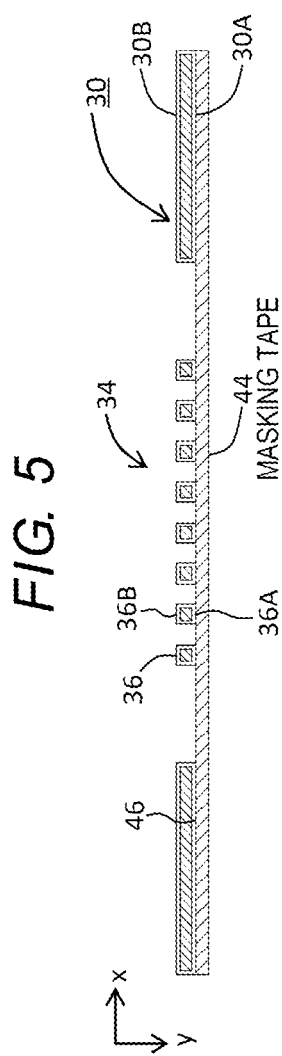
FIG. 5 is a cross-sectional view of a lead frame with an insulating coating, to which a masking sheet is bonded.

Hereinafter, embodiments of the present invention will be described with reference to accompanying drawings.

(1) Summary of Embodiments

An ultrasonic probe according to the embodiment includes a vibration element array and a backing. The vibration element array includes a plurality of vibration elements that are two-dimensionally arranged. The backing includes a plurality of backing plates provided on a rear surface side of the vibration element array. Each backing plate includes a lead row including a plurality of leads electrically connected to the vibration element array, and a main body formed of a backing material and including a plurality of grooves that are directly coupled to the plurality of leads without using an adhesive while accommodating the plurality of leads. Each lead includes a lead wire and an insulating coating wrapping the lead wire.

According to the above configuration, since each lead wire is surrounded by the insulating coating, short-circuit between the leads does not occur or a possibility of generating the short-circuit may be reduced. Accordingly, a filling rate of conductive fillers may be increased. In the backing plate, since the plurality of leads are directly coupled to the plurality of grooves of the plate main body without using an adhesive (or another layer), a usage amount of the adhesive may be reduced and an acoustic characteristic of the backing may be improved.

According to the embodiment, in processes of manufacturing the backing, the backing material flows into a periphery of the lead row so that each lead may be embedded, that is, so that there is no gap generated between each lead and an internal surface of each groove and there is no need to apply the adhesive to the gap. When the backing material is flowed to the entire lead array that is three-dimensionally spread, a concentration gradient in the backing material may occur due to a difference in specific gravities, but by flowing in each lead row in a horizontal attitude, the concentration gradient does not become a problem. In other words, a composition of the backing material may be uniformed for the entire backing. Also, a concept of the two-dimensional vibration element array may include, for example, 1.5D type vibration element array.

In the embodiment, the backing includes an adhesive that bonds the plurality of backing plates to one another, and each insulating coating includes a material that is different from the adhesive. According to the above configuration, a material having an excellent insulating property may be selected as a material of the insulating coating, and a material having a low viscosity and a high adhesive strength may be selected as the adhesive.

In the embodiment, each insulating coating has an exposed surface that is exposed out of each groove, and each backing plate includes a first plane including a plurality of exposed surfaces included in the lead row and a second plane that is in parallel with the first plane. In this configuration, the first plane including the plurality of exposed surfaces configures a reference surface, and the second plane is arranged to be in parallel with the reference surface. Although it is possible to make the lead row completely buried in the backing plate, in this case, it is difficult to determine a shape of the backing plate based on the lead row. On the other hand, the above configuration is to determine the shape of the backing plate based on one side surface of the lead row (in other words, based on the lead row itself).

In the embodiment, each insulating coating has a thickness within a range from 10 to 30 µm. Depending on specific circumstances, a thickness that exceeds or fall below the above numerical range may be also selected.

The method of manufacturing the backing according to the embodiment includes a process of forming a coating, a process of manufacturing a plate, and a laminating process. In the process of forming the coating, the insulating coating is formed on at least a plurality of lead rows included in the plurality of lead frames. In the process of manufacturing the plate, after forming the insulating coating, the plurality of backing plates may be manufactured by pouring the backing material to the lead row so that the lead row of each lead frame may be integrated with the backing material. In the laminating process, the plurality of backing plates are laminated.

In the above configuration, the pouring and molding of the backing material may be performed in units of backing plates. Accordingly, the backing material is integrated with the lead row, and the gap does not generate therebetween. This also reduces a usage amount of the adhesive. In addition, according to the above configuration, since uniformity of the backing material may be ensured at the time of manufacturing in units of the backing plates, the acoustic characteristic of the backing may be improved. Moreover, in the backing, each lead has the insulating coating, and thus, short-circuit between the leads may be prevented or reduced. In other words, electrical characteristics may be improved. Conversely, it may be allowed to increase a filling rate of a conductive filler.

In the embodiment, during the process of manufacturing the plate, for each lead frame, a masking sheet is provided on one side of the lead frame, a mold is provided on the other side of the lead frame, and then, the backing material is poured into a space surrounded by the masking sheet and the mold. According to the above configuration, the backing plate may be manufactured by performing the pouring once.

In the embodiment, the masking sheet has a viscosity, and the backing material may be poured into the space in a state in which the lead row is temporarily fixed on the masking sheet. According to this configuration, deformation of the lead row may be prevented or reduced when the backing material is poured and the backing material is cured.

In the embodiment, during the process of forming the coating, the insulating coating is also formed for the frame body of each lead frame. According to this configuration, forming of the insulating coating may be easily performed.

In the embodiment, each lead has a rectangular cross-section, but the cross-section may be formed in other shapes. According to the pouring method (screen printing method), it may be relatively easy to manufacture the plate main body even when the lead row has various shapes.

(2) Detailed Embodiments

FIG. 1 shows an ultrasonic probe according to an embodiment. The ultrasonic probe 10 shown in FIG. 1 is a transducer that may be used in contact with a surface of a living body (examinee). An ultrasonic wave beam is formed by the ultrasonic probe 10, and the ultrasonic wave beam is electrically scanned two-dimensionally. Then, volume data is obtained from a three-dimensional space in the living body. In other words, the illustrated ultrasonic probe is a 3D probe. The ultrasonic probe 10 is detachably attached to an ultrasonic diagnostic apparatus body (not shown). An ultrasonic diagnostic apparatus includes the ultrasonic probe and the ultrasonic diagnostic apparatus body. The ultrasonic diagnostic apparatus is a medical apparatus used in a medical institution such as a hospital, etc. One or more techniques that are described below may be applied to other ultrasonic probes such as a 3D probe of a body cavity insertion-type, etc.

In FIG. 1, a z direction is a direction in parallel with a probe central axis, and is defined as a vertical direction for convenience of description. An x direction is a first horizontal direction perpendicular to the z direction, and is a di in which a plurality of leads configuring the lead row that will be described later are arranged. A y direction (not shown) is a second horizontal direction perpendicular to the z direction, and a direction, in which a plurality of backing plates that will be described later are arranged, that is, a plate laminating direction.

Specifically, the ultrasonic probe 10 includes a probe head 12, a cable 14, and a connector (not shown). The probe head 12 includes a hollow case 16 that is held by a user. An assembly 18 is arranged in a tip 12a of the probe head 12. The assembly 18 is provided from the living body side to a non-living body side, and includes a laminated body 20, a backing with built-in lead array (hereinafter, simply referred to as 'backing') 22, a relay substrate 24, an electronic circuit 26, etc.

The laminated body 20 includes a two-dimensional vibration element array, a matching layer provided on the living body side, a protective layer provided on the living body side, and a hard backing layer provided on a rear surface side (non-living body side) of the two-dimensional vibration element array. The two-dimensional vibration element array includes a plurality of vibration elements arranged in the x direction and y-direction. The hard backing layer includes a plurality of hard backing elements provided on rear surface sides of the plurality of vibration elements. Each of the hard backing elements includes a conductive member having an acoustic impedance that is higher than that of each vibration element. Regarding this, the backing 22 as a whole may have an acoustic impedance that is lower than that of each vibration element. The backing 22 may be regarded as a soft backing layer as compared with the hard backing layer.

The backing 22 is configured as a plate laminated body including a plurality of backing plates arranged in the y direction. Each backing plate includes a backing material and a lead row. The lead row includes a plurality of leads arranged in the x direction. The lead row according to the embodiment is a lead row with an insulating coating.

The backing material includes a mother material (base material) and one or more fillers added to the mother material. Typical materials included in the base material may include an epoxy resin, a urethane resin, an acryl resin, etc. One or more fillers are added to make an acoustic characteristic of the backing 22 have a desired level. For example, a filler for improving an acoustic impedance, a filler for scattering ultrasonic waves, a filler for absorbing ultrasonic waves, etc. are known. The filler for improving the acoustic impedance or the filler for scattering the ultrasonic waves generally includes a metal material. Examples of the metal may include tungsten, tungsten carbide, tungsten silicide, aluminum oxide, etc. The filler for absorbing may include powder-like silicone, etc.

The backing material includes, for example, an acoustic impedance of 3 to 10 MRayl. Such above acoustic impedance range is lower than the acoustic impedance of the vibration element array. In addition, the backing 22 itself may function as a hard backing. A volume ratio of the filler with respect to the total backing material is 0% to 20%. Materials and numerical values recited in the present specification are examples.

The lead row included in each backing plate includes the plurality of leads arranged in the x direction, and each lead includes a lead wire and an insulating coating wrapping the lead wire. Each lead wire (a lead frame before forming the insulating coating that will be described later) includes, for example, phosphor bronze, copper, aluminum, etc. The insulating coating is formed by an electrodeposition coating method, an electrostatic coating method, CVD method, a sputtering method, etc. Materials constituting the insulating coating may include an acryl resin, a polyimide resin, a urethane resin, a fluororesin, an epoxy resin, etc. A thickness of the insulating coating is in a range of, for example, 10 μm to 30 μm.

The plurality of vibration elements included in the vibration element array and the plurality of leads (lead wires) included in the lead array are electrically connected to each other in one-to-one correspondence. A pitch between the vibration elements and a pitch between the leads are set within a range of, for example, 0.2 mm to 0.4 mm. A length of one side in each lead is set within a range of, for example, 30 μm to 80 μm.

The relay substrate 24 provided between the lead array and the electronic circuit 26 has a function of changing a wiring pattern. The relay substrate 24 is also referred to as an interposer, and includes a multilayer substrate. The electronic circuit 26 includes one or more ICs. The electronic circuit 26 is a circuit for performing a channel reduction by a sub beamforming.

When the plurality of backing plates are bonded, an epoxy adhesive, for example, may be used as an adhesive. Although the material is close to the base material in the backing 22, a material having a low viscosity and a high adhesive strength is used as the adhesive material as compared with the based material. As the base material, a material for setting the acoustic characteristic of the backing 22 as a desired level may be used.

FIG. 2 is a flowchart illustrating a method of manufacturing the backing according to an embodiment. First, the manufacturing method will be briefly described, and then, the manufacturing method will be described in detail with reference to FIGS. 3 to 13.

In FIG. 2, an insulating coating is formed with respect to each of a plurality of lead frames in operation S10. In operation S12, a masking sheet is stuck to one surface of each lead frame. In operation S14, a mold is provided on the other surface (upper surface) of the lead frame in a state in which a side of the masking sheet faces downward. In addition, the backing material having fluidity is poured into a space surrounded by the mold and the masking sheet, and after that, a process of curing the backing material is performed. Accordingly, the plurality of backing plates are manufactured.

In operation S16, a thickness of each backing plate is adjusted. In operation S18, the plurality of backing plates are laminated by using a jig. During or after the lamination process, the adhesive is introduced into each interface. Accordingly, a plate laminated body is formed. In operation S20, the plate laminated body is shaped, and after that, in operation S22, an electrode array is formed respectively on an upper surface (living body side surface) and a lower surface (non-living body side surface) of the plate laminated body. The assembly is made by using the backing manufactured as above, and the assembly is arranged in a probe case.

FIG. 3 shows a result of operation S10, that is, shows a lead frame with the insulating coating (hereinafter, referred to as 'lead frame') 30. As described above, the x direction is the first horizontal direction and the z direction is the vertical direction. The lead frame 30 includes a lead row 34 and a frame body 32 holding the lead row 34. The lead row 34 includes a plurality of leads 36 arranged in the x direction. The number of leads included in the lead row 34 corresponds to the number of vibration elements of the vibration element array in the x direction. Slits 38 are formed between the plurality of leads 36. A pair of openings 40 is formed on opposite sides of the lead row 34 in the x direction. The frame body 32 has a rectangular shape, in which four holes 42 are formed. Each of the holes 42 functions to align the plurality of backing plates.

FIG. 4 shows a cross-section taken along line A-A' of FIG. 3 (xy cross-section). As described above, the lead frame 30 includes the leads 36 and the frame body 32. The frame body 32 is provided with an insulating coating 32a, and each lead 36 is also provided with an insulating coating 36a. Since the frame body 32 is finally removed in the process of manufacturing the backing, the insulating coating 32a may not be formed. However, it is easy to form the insulating coating 32a on the frame body 32 in order to improve a workability when forming the insulating coating. Each of the leads 36 includes, in detail, a lead wire having conductivity and the insulating coating 36a surrounding the lead wire. The xy cross-section of the lead wire is rectangular, and the lead 36 itself including the insulating coating 36a also has a rectangular xy cross-section. Each lead 36 may have a cross-section other than the rectangular shape. For example, the cross-section may have a circular shape. When the lead 36 has the rectangular cross-section, as described later, it becomes easy to manufacture the backing plate based on a certain surface of the lead 36.

FIG. 5 shows a result of operation S12. The lead frame 30 includes a first surface 30A and a second surface 30B, and a masking sheet 44 is stuck to the first surface 30A. An adhesive layer 46 is formed on one surface (upper surface) of the masking sheet 44, and the first surface 30A of the lead frame 30 is detachably bonded to the adhesive layer 46 (temporarily bonded). The masking sheet exerts a function of closing a lower side of the plurality of slits and the pair of openings described above. In addition, at the time of pouring the backing material, and in the curing process after that, the masking sheet 44 also exerts a function of holding the shape and position of the leads so that each of the leads is not easily deformed. In each lead 36, one side surface in the y direction is a first surface 36A and the other side surface in the y direction is a second surface 36B. The first surface 36A is a surface functioning as an exposed surface, that is, a reference surface. The second surface 36B is a surface integrated with the backing material without a gap, together with opposite side surfaces of the lead 36 in the x direction. As the masking sheet 44, for example, an adhesive tape including polyimide may be used.

FIG. 6 shows a preparing step before performing operation S14. The lead frame 30, to which the masking sheet 44 is stuck, has a horizontal posture, and a mold (stencil) 48 is provided on an upper side thereof. The mold 48 has an opening portion 50 of a rectangular shape. A concave portion surrounded by the mold 48 and the masking sheet 44 becomes a pouring space 52. In FIG. 6, the second surface 30B is partially exposed in the opening portion 50, and all of the pair of openings are blocked by the backing material. However, the pair of openings may be blocked by the backing material except for a part in the pair of openings.

FIG. 7 shows an upper surface of the lead frame on which the mold 48 is arranged. In FIG. 7, a cross-section taken along line B-B' corresponds to the cross-section shown in FIG. 6. The pouring space 52 covers the plurality of slits 38 and the pair of openings 40. The masking sheet is exposed through the slits and openings (see reference numeral 44'). Reference numeral 54 indicates a direction, in which a squeegee (surface leveling member) is moved (clearing direction), at the time of pouring the backing material.

FIG. 8 shows a process of executing operation S14 (pouring step). While pouring a backing material 56 before being cured into the pouring space 52 or after the pouring, the backing material 56 is levelled by using a squeegee 58 so that a surface of the backing material 56 may be at the same level as that of a surface of the mold 48, and at the same time, an excessive portion of the backing material 56 may be expelled to outside. After that, the backing material 56 is heated to be cured. Accordingly, the backing plate (here, its original shape) is manufactured. After curing the backing material, the mold and the masking sheet are removed.

FIG. 9 shows a state before executing operation S16. The backing plate 62 includes a plate main body 64 obtained from the backing material after being cured, and the lead frame 30. The lead row 34 of the lead frame 30 is embedded in the plate main body 64 while exposing one surface thereof. In the plate main body 64, a groove row 68 is formed to correspond to the lead row 34. The groove row 68 includes a plurality of grooves 70 corresponding to the plurality of leads 36. Each of the grooves 70 is generated as a result of filling the backing material away from each lead 36. Each lead 36 has a rectangular cross-section, and each groove 70 may also have a rectangular cross-section. Among four side surfaces that each lead has, a side surface facing downward in FIG. 9 is the exposed surface (first surface) 36A. Since the lead row 34 has the plurality of leads, the lead row 34 as a whole includes a plurality of exposed surfaces 36A. Reference numeral 66 indicates a temporary thickness of the backing plate 62.

The backing plate 62 includes a first surface 62A corresponding to a lower surface shown in FIG. 9, and a second surface 62B corresponding to an upper surface shown in FIG. 9. The first surface 62A is a plane including the exposed surfaces 36A of the plurality of leads 36 and the exposed surface of the frame body. The first surface 62A functions as a reference surface as described below.

Figure 10:
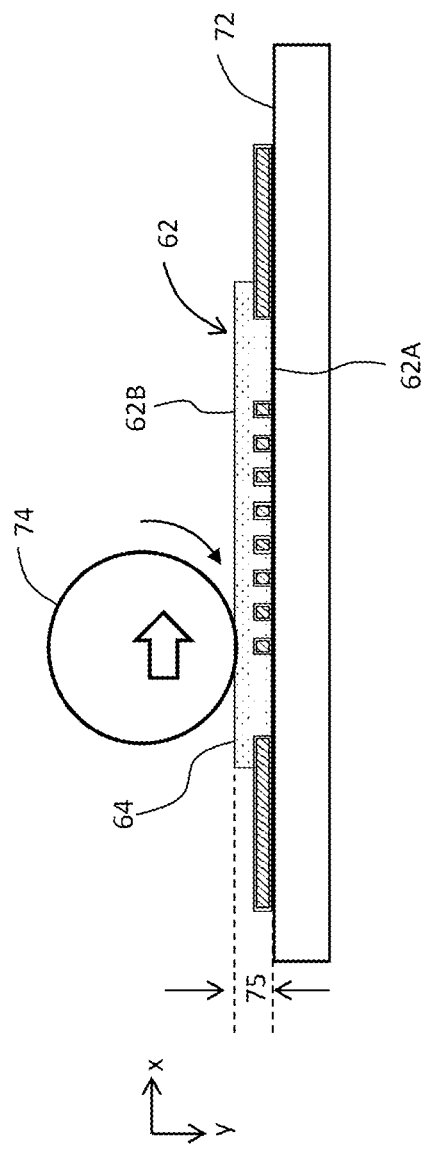
FIG. 10 is a diagram illustrating a method of adjusting a thickness of a backing plate.

FIG. 10 shows a process of executing operation S16. The backing plate 62 is arranged on a pedestal 72. The pedestal 72 has an adsorbing function. The first surface 62A of the backing plate 62 is adsorbed on an upper surface of the pedestal 72. A height and inclination of the second surface 62B are adjusted based on the first surface 62A. In particular, the second surface 62B is cut or ground so that the backing plate 62 may have a predetermined thickness 75 and the second surface 62B may be in completely parallel with the first surface 62A. In this case, for example, a surface grinder 74 may be used. Since one surface of the lead frame is exposed in the first surface 62A, one surface of the lead frame functions as a reference surface. The above masking sheet may be considered as a reference surface and a protecting member of the insulating coating. As a result of executing operation S16, the plurality of backing plates 62 having a predetermined thickness may be manufactured. However, in this process, each backing plate 62 includes the frame body in which four holes are formed.

FIG. 11 shows a process of executing operation S18. A jig 76 includes a base 78 and four pins 80, and the plurality of backing plates 62 are sequentially laminated so that the four pins 80 may penetrate through the four holes 42. For example, the backing plates 62, the number of which corresponds to the number of vibration elements arranged in the y direction of the vibration element array, are laminated. If necessary, an end plate 82 may be also arranged. The adhesive is introduced between the backing plates during the laminating process, or the adhesive is introduced between the backing plates after finishing the lamination. In this case, a plate laminated body 86 may be arranged in a vacuum chamber, if necessary. A complete bonding state (thermosetting state) may be obtained by performing a heating process while pressurizing (84) the plate laminated body 86.

FIG. 12 shows the plate laminated body 86 after being thermally cured. In above operation S20, except a portion surrounded by a cutting line 88, the remaining portion is removed. That is, the frame body, etc. are removed from each lead frame.

FIG. 13 shows a plate laminated body 90 after shaping. (A) illustrates a top view, (B) illustrates a first side view, and (C) illustrates a second side view. In above operation S22, electrode arrays are respectively formed with respect to upper and lower surfaces (two surfaces perpendicular to each other in the z direction) of the plate laminated body 90. Accordingly, the backing is completed. The electrode array may be formed by a deposition method, a sputtering method, a plating method, etc. The lead array is included in the backing. The lead array includes the plurality of lead rows arranged in the y direction. The electrode array includes a plurality of electrodes corresponding to the plurality of leads in the lead array.

Next, operational effects of the insulating coating will be described with reference to FIGS. 14 and 15. FIG. shows an xz cross-section of the backing (vertical section). Each lead 36 includes the lead wire 36b and the insulating coating 36a wrapping the lead wire 36b, as described above. A backing material 92 includes a mother material (base material) 94 and fillers 96. Some of the fillers 96 has a conductivity. For example, as shown exaggeratedly in FIG. 14, although a connected body 98 in which a plurality of filler particles are connected between two leads 36 happens to be generated, because the insulating coating 36a exists, electric short-circuit does not occur between two lead wires 36b. An electrical insulating property may be improved. In other words, the filling rate of the conductive filler may be improved.

FIG. 15 shows an xy cross-section of the backing (horizontal section). Reference numeral 100 indicates an interface between two neighboring backing plates (plate main body). Each lead 36 has a rectangular cross-section. The lead wire 36b includes four side surfaces 104a, 104b, 104c, and 104d, which are surrounded by the insulating coating 36a. The insulating coating 36a includes four external surfaces 106a, 106b, 106c, and 106d. Each groove 70 has the same shape as that of each lead 36, and has internal surfaces 108a, 108b, and 108c. Although the interface 100 is configured as an adhesive layer, the external surfaces 106a, 106b, and 106c of each insulating coating 36a and the internal surfaces 108a, 108b, and 108c of each groove 70 are completely coupled to and integrated with each other, and thus the adhesive layer (and other layers) does not exist between them. The external surface (exposed surface) 106d of each insulating coating 36a is only bonded to the adhesive layer as the interface 100.

As described above, according to the present embodiment, three side surfaces, except the exposed surface, of each lead are in close contact with three internal surfaces in each groove of the plate main body, and there is no gap between them. That is, since the adhesive layer does not exist between them, the usage amount of the adhesive throughout the entire backing may be reduced. Accordingly, the acoustic characteristic of the backing may be improved. In addition, even when the metal is ionized due to the moisture, etc. on opposite sides of the interface 100 (ion migration), the insulating coating 36a is provided on each lead 36, and thus, generation of electric short-circuit may be effectively suppressed.

Figure 16:
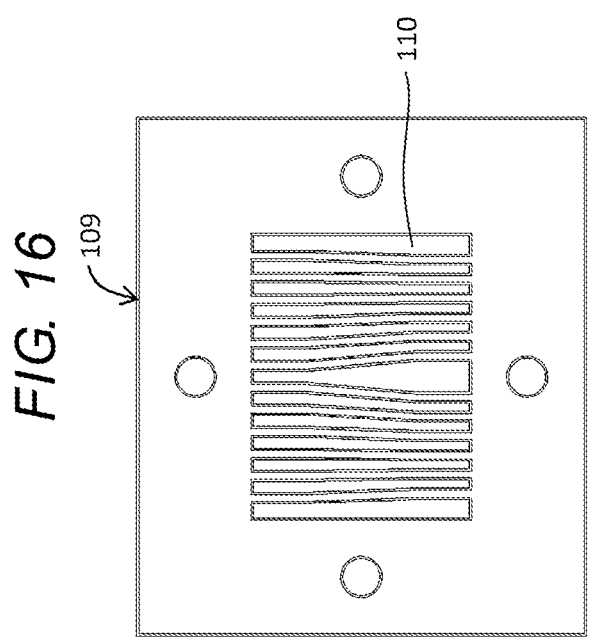
FIG. 16 is a diagram showing a modified example of a lead frame with an insulating coating.

FIG. 16 shows a modified example of a lead frame. A lead frame 109 shown in the drawing is a lead frame with an insulating coating, and includes a lead row 110 of a non-linear type. For example, when an arrangement conversion is to be performed in the backing, the lead row 110 may be used. In the above lead frame 109, the backing plate may be also easily manufactured by the screen printing method like in the lead frame shown in FIG. 3.

Figure 17:
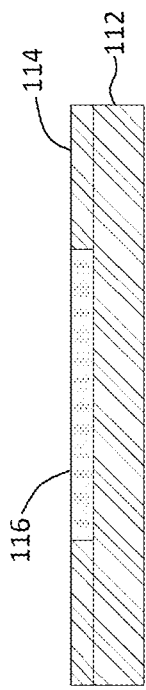
FIG. 17 is a diagram showing a modified example of a screen printing method, and shows a cross-section of a first layer in a backing plate.
Figure 18:
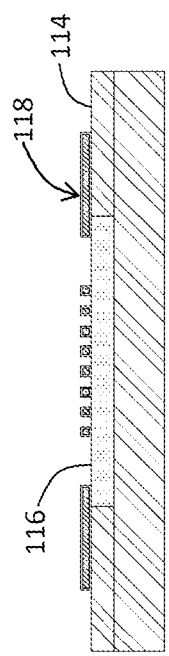
FIG. 18 is a diagram showing a modified example of a screen printing method, and shows a cross-section of arrangement of a lead frame with an insulating coating.
Figure 19:
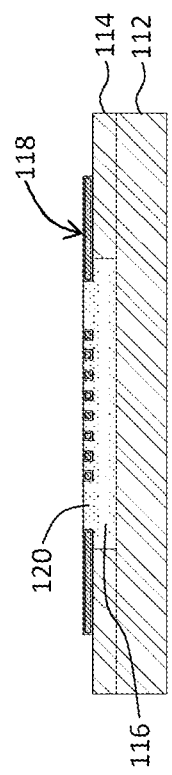
FIG. 19 is a diagram showing a modified example of a screen printing method, and shows a cross-section of a second layer in a backing plate.

Next, a modified example of the method of manufacturing the backing plate will be described with reference to FIGS. 17 to 19. In FIG. 17, a mold 114 is provided on a pedestal 112. The mold 114 includes an opening portion, in which a backing material 116 may be poured. The backing material 116 constitutes a first layer in a plate main body. A curing process is performed with respect to the backing material 116. After that, as shown in FIG. 18, a lead frame 118 is placed on an upper surface of the mold 114. The lead frame 118 is, for example, the lead frame with the insulating coating shown in FIG. 3. Next, as shown in FIG. 19, a backing material 120 is poured towards a plurality of slits and a pair of openings included in the lead frame 118. The backing material 120 is the same as the backing material 116 that is previously poured, and constitutes a second layer in the plate main body. A curing process is performed with respect to the backing material 120. The first layer and the second layer configure the plate main body.

After curing the backing material 120, the backing plate is formed by removing the pedestal 112 and the mold 114. The above backing plate corresponds to the backing plate before the thickness adjustment as shown in FIG. 9.

According to the modified example illustrated with reference to FIGS. 17 to 19, the backing plate may be also manufactured by the screen printing method. In the present modified example, the second layer is formed before curing the first layer, and then both of the first and second layers may be cured at once. Alternatively, the first layer and the second layer may be formed at the same time. In this case, a member integrating the pedestal 112 and the mold 114 may be used. However, when there is a possibility that a variation in the position and the shape of each lead becomes a problem at the time of pouring the backing material, it is desirable to use the above mentioned screen printing technique that uses a masking tape having a viscosity. In any case, according to the above embodiment, the backing having superior electrical and acoustic properties may be manufactured, and the backing may be incorporated into the ultrasonic probe.

What is claimed is:

1. A method of manufacturing a backing, comprising:
   a coating forming process, in which insulating coatings are formed with respect to at least a plurality of lead rows included in a plurality of lead frames;
   after the forming of the insulating coatings, a plate manufacturing process, in which a plurality of backing plates are manufactured by pouring a backing material towards a lead row in each of the plurality of lead frames so that the lead row and the backing material are integrated with each other; and
   a laminating process, in which the plurality of backing plates are laminated; wherein
   in the plate manufacturing process, for each lead frame, a masking sheet is provided on one side of the lead frame, and a mold is provided on the other side of the lead frame, and the backing material is poured into a space surrounded by the masking sheet and the mold.

2. The method of manufacturing a backing of claim 1, wherein
   the masking sheet has viscosity, and
   the backing material is poured into the space in a state in which the lead row is temporarily fixed on the masking sheet.

3. The method of manufacturing a backing of claim 1, wherein
   in the coating forming process, the insulating coating is formed also with respect to a frame body in each lead frame.

* * * * *